(12) United States Patent
Bosio

(10) Patent No.: US 7,554,657 B2
(45) Date of Patent: Jun. 30, 2009

(54) ACCOMODATING DEVICE FOR SPECIMEN SLIDES

(75) Inventor: Andreas Bosio, Köln (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 11/580,378

(22) Filed: Oct. 13, 2006

(65) Prior Publication Data

US 2007/0030480 A1 Feb. 8, 2007

Related U.S. Application Data

(63) Continuation of application No. 10/472,134, filed as application No. PCT/EP02/02889 on Mar. 15, 2002, now abandoned.

(30) Foreign Application Priority Data

Mar. 16, 2001 (DE) .................................. 101 12 682

(51) Int. Cl.
*G01N 21/01* (2006.01)
(52) U.S. Cl. ...................................................... 356/244
(58) Field of Classification Search .......... 356/244–246
See application file for complete search history.

(56) References Cited

U.S. PATENT DOCUMENTS

| 2,761,558 | A | | 9/1956 | McLean, Jr. ................. 206/62 |
| 3,746,161 | A | | 7/1973 | Jones ........................ 206/72 |
| 3,951,512 | A | | 4/1976 | Tolles ........................ 350/90 |
| 4,159,875 | A | | 7/1979 | Hauser ...................... 356/244 |
| 4,209,923 | A | * | 7/1980 | Wendt ........................ 40/710 |
| 4,589,551 | A | | 5/1986 | Hellon ...................... 206/456 |
| 4,836,667 | A | | 6/1989 | Ozeki ....................... 350/531 |
| 5,439,649 | A | | 8/1995 | Tseung et al. .................. 422/99 |
| 5,641,683 | A | | 6/1997 | Van Dusen et al. ............ 436/46 |
| 6,118,582 | A | | 9/2000 | Del Buono ................. 359/398 |

FOREIGN PATENT DOCUMENTS

| EP | 1 798 550 A1 | 10/1997 |
| GB | 2009045 | 6/1979 |

* cited by examiner

*Primary Examiner*—Michael P Stafira
(74) *Attorney, Agent, or Firm*—Ohlandt, Greeley, Ruggiero & Perle, L.L.P.

(57) ABSTRACT

A receiving device for object holders comprises a base part. A plurality of centering elements are connected with the base part. The centering elements are arranged such that a plurality of receiving areas for receiving one object holder each are configured. The centering elements form a preferably circumferential centering frame around each receiving area.

11 Claims, 3 Drawing Sheets

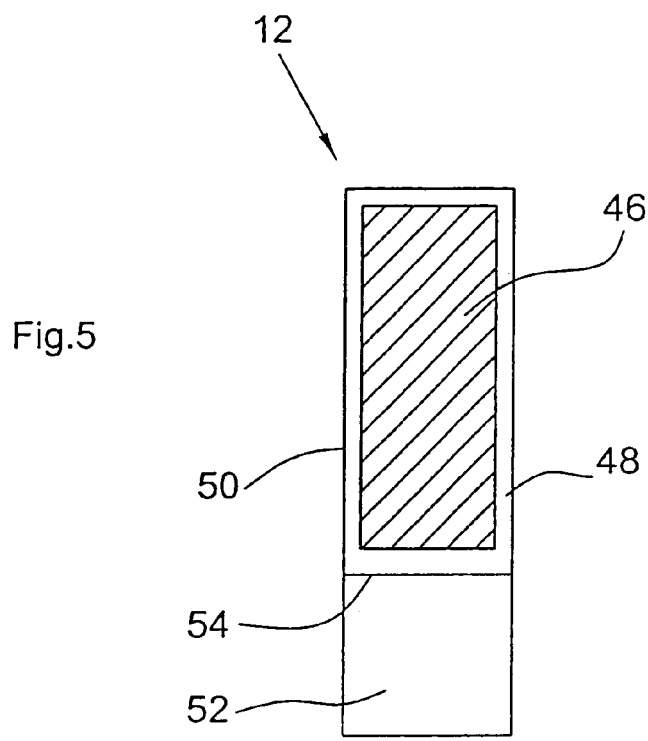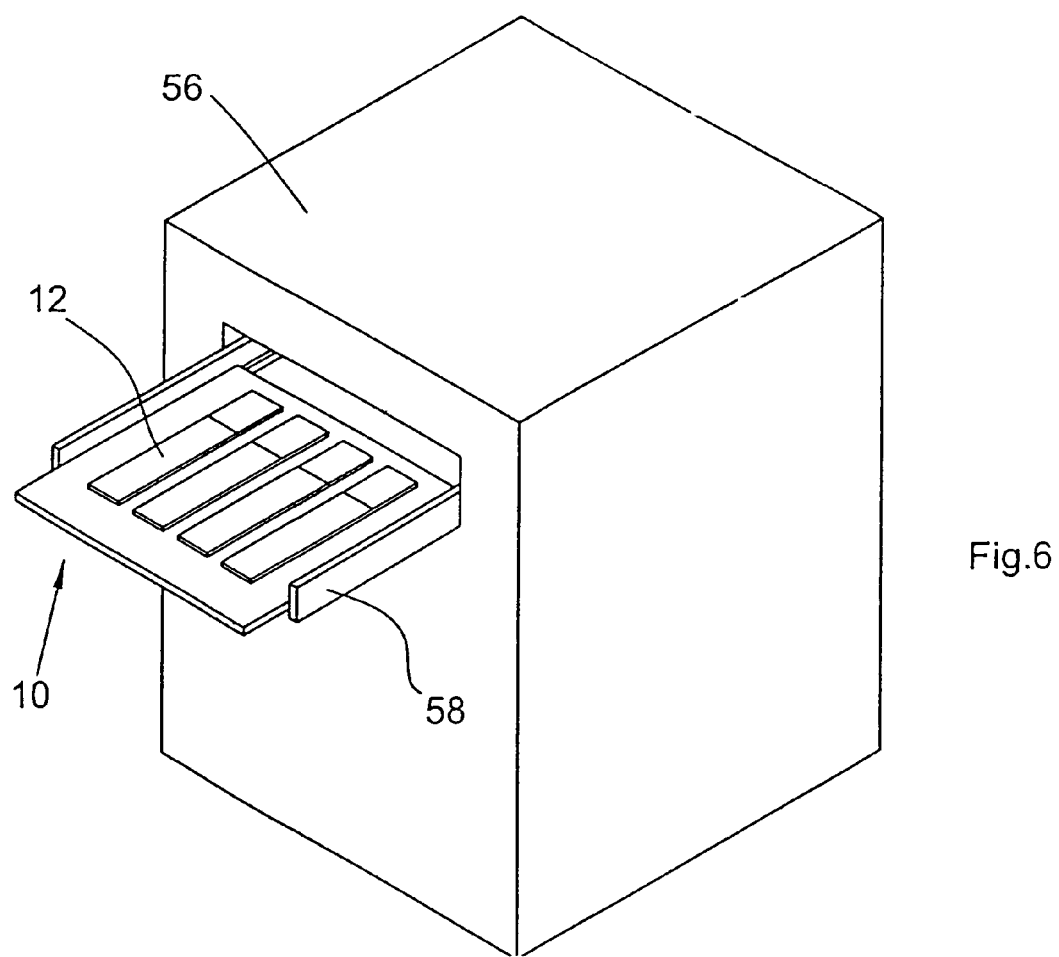

ACCOMODATING DEVICE FOR SPECIMEN SLIDES

CROSS REFERENCE TO RELATED APPLICATIONS

This application is a continuation of U.S. application Ser. No. 10/472,134 filed Feb. 25, 2004 now abandoned, which is a national stage application of International Application No. PCT/EP02/02889 filed on Mar. 15, 2002 and German Application No. 101 12 682.4 filed on Mar. 16, 2001.

BACKGROUND OF THE INVENTION

1. Field of the Invention

The invention relates to a receiving device for object holders.

2. Description of Related Art

Object holders are e. g. thin-glass plates upon which samples to be analyzed are arranged. Frequently, two such object holders are placed one upon the other such that the sample to be analyzed, which in particular is a sample liquid, is located between two object holders. Object holders may further be titer plates or similar plates provided with recesses for receiving individual samples.

For example, object holders are used for analyzing tissue samples. In this connection, DNA pieces, for example, i.e., gene fragments, are applied upon the surface of an object holder. Applying the DNA pieces is effected by dripping by means of a robot. Thus, the position of the individual DNA pieces on the object holder is known. The DNA pieces connect with the surface of the object holder and adhere thereto so that their positions do not change in the subsequent analyzing process.

From a tumor to be examined, for example, RNA is taken in the next step. By means of enzymes, the RNA is transformed into DNA and subsequently marked with suitable markers, particularly fluorescent color markers.

Additionally, a comparative sample with healthy tissue is produced. The healthy DNA is also marked with a suitable marker. Preferably, the marker is a fluorescent marker of another color so that the healthy tissue is marked with a greenly fluorescent marker and the tissue to be analyzed taken from the tumor, for example, with a red color marker.

Subsequently, both samples are applied onto the entire object holder. The DNA strands included in the two samples firmly connect to the counterparts, i.e., the DNA pieces present on the surface of the object holder. Connecting the DNA included in the samples with the DNA pieces adhering to the object holder is effected in a hybridization process. Subsequently, the object holder is washed so that only firmly adhering DNA pieces and chained-up DNA from the two samples is present on the object holder.

After the object support has been dried, it is put to a detecting process. Therein, the individual positions of the object holder to which DNA pieces adhere are analyzed by a suitable microscope. In doing so, the individual DNA pieces are stimulated by laser light, for example, so that the fluorescent markers fluoresce in the corresponding color. If a certain position to which a DNA piece adheres appears as a red spot, for example, it can be concluded therefrom that this gene was active in the tumor tissue but not in the healthy tissue. If a spot fluoresces greenly, it can be concluded. therefrom that this gene was only active in the healthy tissue. In the case of yellow fluorescence occurring, the corresponding gene was active in both tissues. By the above method, it can be diagnosed which genes are active in a tumor, for example. Therefrom, conclusions as to the kind of tissue change and the like can be drawn.

In such processes, in particular the handling of individual object holders is difficult. Particularly, object holders of thin glass can easily break. Further, when handling object holders, it must be ensured that areas to which samples are applied are not touched. For this reason object holders are difficult to align in the corresponding analyzing devices.

BRIEF SUMMARY OF THE INVENTION

It is an object of the invention to improve the handling of object holder.

For improving the handling of object holders the invention provides a receiving device for object holders. Said receiving device comprises a base part onto which preferably a plurality of object holders can be placed side by side. According to the invention, centering elements are connected with the bottom part. Said centering elements are arranged such that a plurality of receiving areas for receiving one object holder each are configured.

Thus, one object holder to which DNA pieces already adhere at predetermined positions, for example, can be laid in the receiving areas of the receiving device, respectively. Then, the receiving device carrying several object holders can be easily handled by means of robot grip arms or the like, for example. Since the receiving device can be easily gripped at the centering elements or at the base part, for example, handling the object holder is easily possible. By the device according to the invention, it is particularly ensured that object holders of thin glass are not damaged during handling. Touching the samples already located on the object holders is avoided as well.

In a first preferred embodiment of the receiving device according to the invention, the base part is a bottom part which is preferably of continuous configuration. Centering elements are connected with the bottom part and define a plurality of receiving areas.

Preferably, the centering elements are configured like integral frame parts. Thus, each object holder is surrounded by a frame. This has the advantage that the object holder is disposed in the receiving area in a protected manner. Preferably, the frame part has a height higher than the thickness of the object holder so that the object holder is received completely within the frame part. Thereby, damaging the object holder upon handling the receiving device as well as touching the surface of the object holder are avoided. Preferably, several receiving areas are formed by a single frame part. In this case, each receiving area is completely surrounded by a frame. A wall of the frame part provided between two neighboring object supports thus serves as portion of the frame of two receiving areas.

Each of the above-described frame parts may surround a receiving area, preferably completely as a circumferential centering frame. But they may also be individual frame parts not surrounding the receiving areas but only serving, for example, to receive corners of the object holder to center the latter in the receiving device. In this case, inserting the object supports into the receiving device is possibly made easier. For making the insertion of the object holders into the receiving device easier, the centering elements may further be chamfered. The chamfer is configured such that the receiving area in which one object holder is respectively received is enlarged upwards to make the insertion of an object holder easier.

In a particularly preferred embodiment the bottom part is made, at least in the receiving area, of a flexible material. In particular the overall bottom part is made of a continuous flexible material. The object holders rest on this flexible material. The use of flexible material offers the advantage that, if e. g. the object holders are touched by pipettes or the like, a certain degree of resilience of the object holders is ensured. This reduces the risk of damage to the object holders during the analyzing process. Further, it is possible to align the object holder e. g. horizontally, wherein e. g. suitable aligning elements press from below against the diaphragm thus changing the position of the object holder. In this way a very accurate alignment of the object holder can be achieved without the need of touching the object holder. In particular, it is e. g. also possible to slightly lift the object holder from below with the aid of a suitable device and e. g. press the object holder against a second object holder plate.

The flexible material is particularly a diathermic diaphragm. Thereby, it is possible to provide heating elements, such as Peltier elements, below the individual receiving areas to heat individual object holders. By means of the receiving device according to the invention a very specific heating of possibly only individual partial regions of an object holder is possible without having to handle the object holder directly. In this case, damaging the object support is again avoided. Preferably, the diaphragm is designed such that temperatures of 4.degree. C. to 100.degree. C. can be transferred to the object support.

In another preferred embodiment the base part has a frame-shaped configuration. The base part comprises receiving areas for receiving a plurality of object holders. The base part is e. g. a rectangular frame divided into receiving areas by a plurality of intermediate webs. The receiving areas are essentially rectangular and have dimensions which are slightly smaller than the dimensions of standard object holders such that the object holders can be inserted into the receiving areas where they rest on the frame-shaped base part.

Preferably, centering element in the form of spring elements are provided on the frame-shaped base part for the purpose of supporting the object holders. Said spring elements serve for clamping the object holders and fixing them in their position. It is possible to configure all centering elements as spring elements such that the object holders are supported in one plane. In this case the object holders are clamped between the spring elements.

Preferably, only some of the centering elements are configured as spring elements. In this embodiment, the remaining centering elements are configured as stop elements. By cooperation of the spring elements with the stop elements the object holder is fixed in its position in the individual receiving areas. In this case the spring elements press the object holder against correspondingly arranged stop elements. For example, spring elements are provided which, in a horizontal plane, press the object holders in x- and y-direction against the stop elements which are essentially aligned perpendicularly to the x- and y-direction. In this case preferably one spring element for each direction and one stop element for each direction are provided. A more accurate and defined fixing in position can be attained if, in particular at the longitudinal side of rectangular object holders, two spring elements are provided which preferably press the object holder against two stop elements aligned perpendicularly to this direction.

The spring elements preferably are projections resiliently connected with the base part. In particular, the spring elements and the base part are integrally formed with each other, wherein said integral part preferably is an injection molded part. Said injection molded part preferably also comprises the stop elements.

To be able to use the receiving device according to the invention particularly in existing arrangements, the outer dimensions of the receiving device correspond to standard dimensions of microtiter plates. The receiving device has a width of 96.+−0.4 mm and a length of 148.+−0.4 mm in particular.

BRIEF DESCRIPTION OF THE SEVERAL VIEWS OF THE DRAWINGS

Hereinafter, the invention will be explained in detail with respect to a preferred embodiment with reference to the accompanying drawings. In the Figures:

FIG. 5 shows a single object holder being adapted to be inserted into the receiving device illustrated in FIG. 1, and FIG. 6 is a schematic perspective view of an analyzing device which is adapted to be inserted into the receiving device.

DETAILED DESCRIPTION OF THE INVENTION

Figure 1:
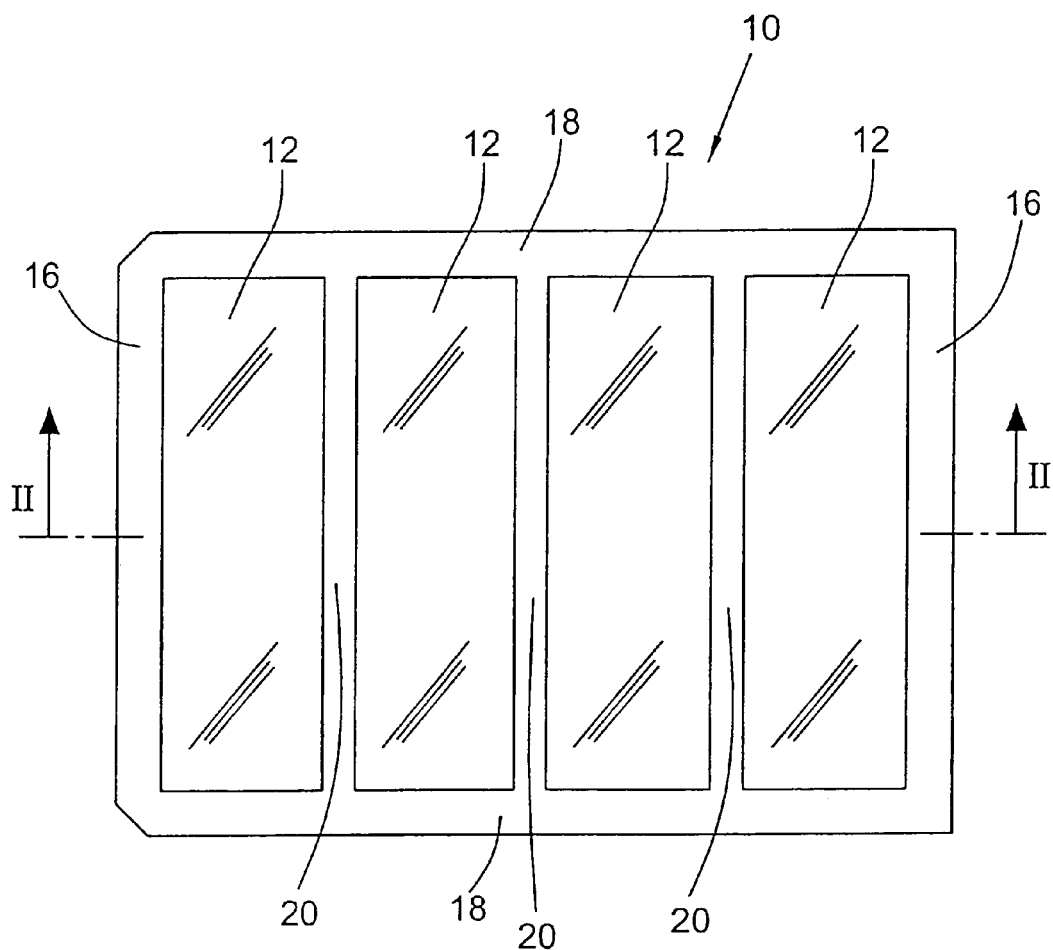
FIG. 1 is a schematic top view of a preferred embodiment of the receiving device according to the invention.
Figure 2:
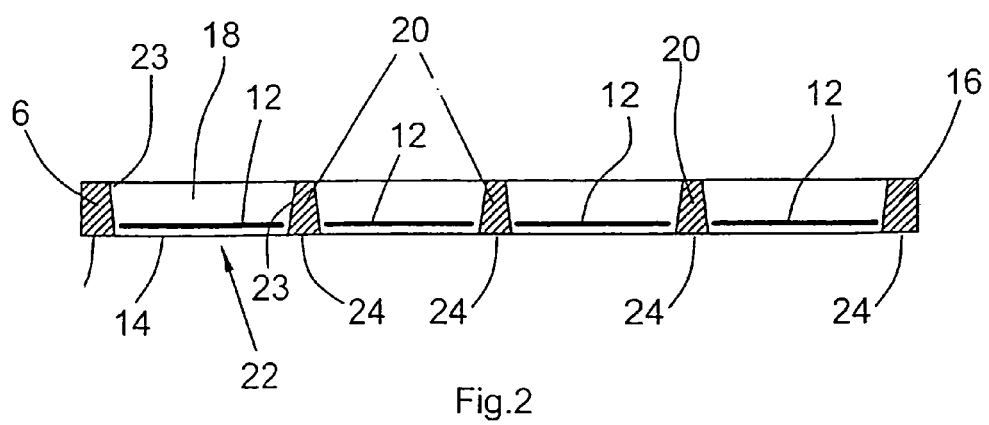
FIG. 2 is a schematic sectional view along the line II-II in FIG. 1.

A receiving device 10 for several object holders 12 comprises a bottom part 14 (FIG. 2). The bottom part 14 is connected with centering elements 16,18,20. In the illustrated embodiment, the centering elements 16,18,20 are arranged such that four rectangular receiving areas 22 are formed in each of which one object holder 12 can be arranged. The centering elements 16,18,20 have two opposing shorter side walls 16 and two also opposing longer side walls 18 arranged between the side walls 16. In the illustrated embodiment, three partition walls 20 arranged in parallel to the shorter side walls 18 are provided between the side walls 18.

At the undersides 24 of the centering elements 16,18,20, the bottom part 14 configured as a diaphragm is mounted. The receiving areas 22 hence have a flexible diaphragm as a bottom on which one object holder 12 is respectively supported. Thus, it is possible to press from below against the diaphragm in FIG. 2 in order to horizontally align the object holder, for example. Further, a heating element can be placed against the object support 12 from below. Due to the flexibility of the diaphragm, the object holder 12 flatly lays against the surface of a flat heating element. Thereby, a uniform and good heat transmission between the heating element and the object holder is ensured.

At their insides 23, i.e. at the sides pointing toward the receiving areas 22, the centering elements 16,18,20 are chamfered. Thereby, the opening of the individual receiving areas pointing upwards in FIG. 2 is upwardly enlarged. This makes the insertion of the object holders 12 into the receiving areas 22 easier.

Figure 3:
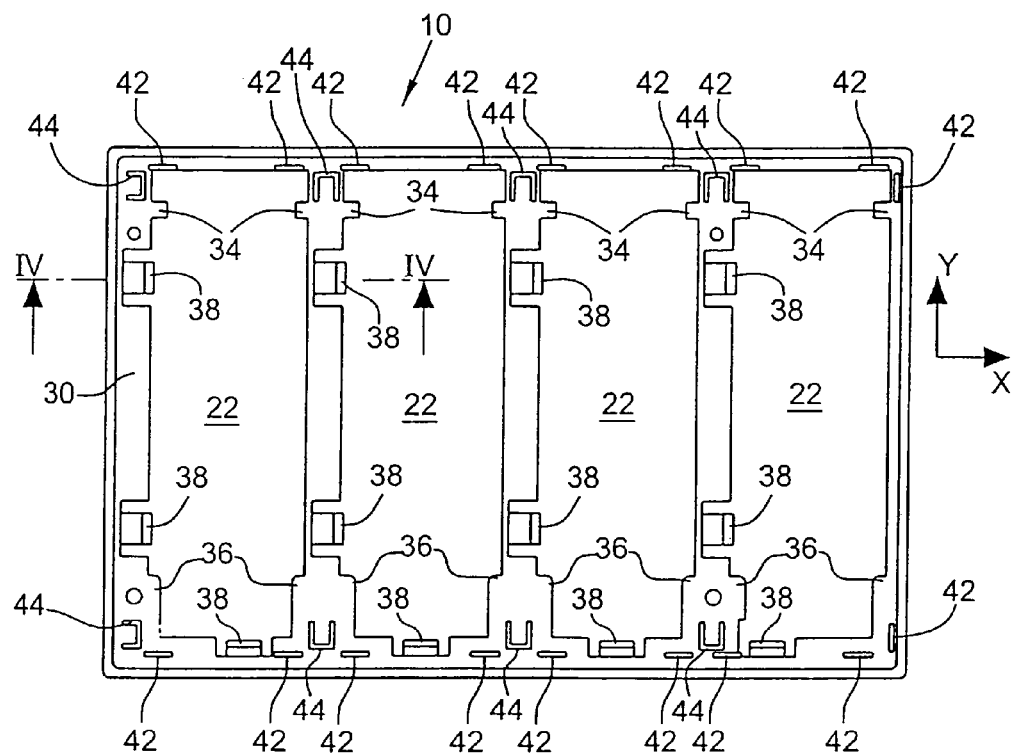
FIG. 3 is a schematic top view of another preferred embodiment of a receiving device according to the invention.
Figure 4:
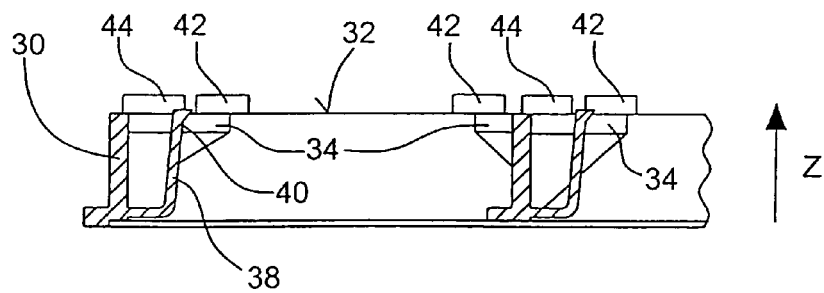
FIG. 4 is a schematic sectional view along the line IV-IV in FIG. 3.

In the second preferred embodiment of the receiving device according to the invention shown in FIGS. 3 and 4 identical or similar components are designated with the same reference numerals.

In the receiving device shown in FIGS. 3 and 4 no object holders 12 are arranged in the individual receiving areas 22. In FIG. 4 these object holders 12 are placed from the top. For this purpose a frame-shaped base part 30 comprises a flat upper side 32 onto which the object holders 12 are placed.

Supporting projections 34 are provided for reliably supporting the object holders, said supporting projections 34 projecting into the receiving areas 22 which are configured as through openings. Further supporting projections 36 are provided which, for reasons of manufacture, span over a corner area of the receiving area 22. Said projections 36 may also be configured in accordance with the supporting projections 34.

For accurately fixing an object holder 12 in position on the upper side 32 of the frame-shaped base part 30 the frame-shaped base part 30 comprises spring elements 38 as centering elements. Said spring elements 38 are integrally formed with the base part 30. Since the base part 30 and the spring elements 38 are preferably made of a plastic material, in particular by applying the injection molding process, the spring elements 38 have a certain degree of resilience. Further, the spring elements 38 have a bevelled leading edge 40 by means of which the object holders resting on the upper side 32 are pressed downwards in FIG. 4. Thus the position of the object holders is also fixed in the z-direction in FIG. 4.

Further, for fixing the object holders in position on the upper side 32 of the base part 30 centering elements configured as stop elements 42,44 are provided. In FIG. 2 the spring elements 38 press an object holder in x- and y-direction, wherein two spring elements 38 are provided at the longitudinal side of an object holder 12. Opposite said spring elements 38 two stop elements 44 are provided against which the object holders are pressed in x-direction. In FIG. 3 the lower spring element 38 presses the object holder in y-direction against the two stop elements 42. The remaining stop elements 42 and 44 are safety stop elements which define, inter alia, the area onto which the object holders 12 are placed.

The individual object holders 12 serve, for example, for analyzing DNA samples. To this end, each object holder, as illustrated in FIG. 5, is divided into different areas. In an inner area 46, sample droplets are applied, for example, which then firmly connect to the sample holder 12. Thus, the area 46 serves as a surface for arranging an array. The area 46 is surrounded by a preferably 2.5 mm wide margin 48. The margin 48, for example, ensures that all the samples provided in the area 46 have a sufficient distance to the outer edges 50 of the object holder 12. Further, seals of a washing head or the like lowered to the object holder 12 can e. g. be arranged in the area of the margin 48. An area 52 separated from the margin 48 by the line 54 illustrated in FIG. 3 serves to touch the sample holder. In this area, no samples are disposed so that the object holder can be handled in this area. The touch area is required, for example, to be able to insert the object holder into the receiving device according to the invention.

The receiving device 10 according to the invention can be inserted into an analyzing device 56 (FIG. 4) comprising e. g. an hybridization head. To this end, the analyzing device 56 comprises a drawer-like receiving means 58 for receiving the receiving device 10. The drawer may be configured in correspondence with a drawer of a CD player or the like. When the drawer is open, the receiving device 10 supporting the object holders 12 is inserted into the drawer from above and then displaced into the analyzing device 56.

The invention claimed is:

1. A receiving device for an object holder, comprising:
   a continuous bottom part, and
   frame parts connected with said bottom part, wherein said frame parts are arranged such that a plurality of receiving areas are configured for receiving one object holder each, wherein said frame parts are configured as centering elements, wherein the bottom part is, at least in the receiving areas, made of a flexible diathermic diaphragm; wherein the outer dimensions of the receiving device comprise the standard dimensions of a titer plate.

2. The receiving device according to claim 1, wherein the centering elements are formed by integral frame parts.

3. The receiving device according to claim 2, wherein a single frame part defines a plurality of receiving areas.

4. The receiving device according to claim 1, wherein the centering elements are chamfered in the direction of the receiving area.

5. The receiving device according to claim 1, wherein the bottom part is configured as a continuous bottom part.

6. The receiving device according to claim 1, wherein at least some of the centering elements are configured as spring elements.

7. The receiving device according to claim 6, wherein some of the centering elements are configured as stop elements for fixing the object holders in position, and cooperate with the spring elements.

8. The receiving device according to claim 6, wherein the spring elements are projections elastically connected with the base part.

9. The receiving device according to claim 1, wherein a plurality of supporting projections for supporting object holders project into the receiving area.

10. The receiving device according to claim 1, wherein at least two receiving areas are provided.

11. The receiving device according to claim 1, wherein the receiving device is configured as an injection molded part.

* * * * *